United States Patent [19]

Nishiyama et al.

[11] 4,203,758
[45] May 20, 1980

[54] HERBICIDAL PHENOXY-PHENOXYALKANE THIO ESTERS

[75] Inventors: Ryuzo Nishiyama, Takatsuki; Ryohei Takahashi, Tokyo; Kanichi Fujikawa, Kyoto; Isao Yokomichi, Kusatsu; Itaru Shigehara, Kusatsu; Nobuyuki Sakashita, Kusatsu, all of Japan

[73] Assignee: Ishihara Sangyo Kaisha Limited, Osaka, Japan

[21] Appl. No.: 837,815

[22] Filed: Sep. 29, 1977

Related U.S. Application Data

[62] Division of Ser. No. 722,327, Sep. 10, 1976, Pat. No. 4,070,177.

[30] Foreign Application Priority Data

Sep. 27, 1975 [JP] Japan .................................. 50-115982
Mar. 5, 1976 [JP] Japan .................................. 51-23084
Mar. 17, 1976 [JP] Japan .................................. 51-28189

[51] Int. Cl.² ...................... A01N 9/12; C07C 153/07
[52] U.S. Cl. .................................. 71/100; 260/455 R
[58] Field of Search .................. 260/465 F, 455 R; 71/105, 100

[56] References Cited

U.S. PATENT DOCUMENTS

| 3,773,945 | 11/1973 | Baklien et al. | 260/455 R |
| 3,954,442 | 5/1976 | Becker et al. | 260/455 R |
| 4,070,178 | 1/1978 | Johnson et al. | 260/465 F |

*Primary Examiner*—Dolph H. Torrence
*Attorney, Agent, or Firm*—Oblon, Fisher, Spivak, McClelland & Maier

[57] ABSTRACT

A herbicide which comprises a compound as an active ingredient having the formula

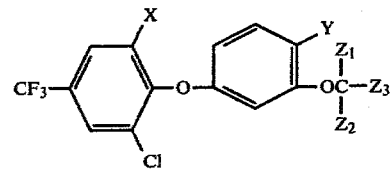

wherein X represents —H or —Cl; Y represents halogen atom or cyano group; $Z_1$ represents —H or methyl group; $Z_2$ represents —H, methyl or ethyl group; $Z_3$ represents cyano group or

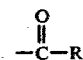

group;

R represents hydroxy group, —O— cation group, $C_1$–$C_4$ alkylthio group, $C_2$–$C_4$ alkenylthio group, $C_2$–$C_4$ alkynylthio group, $C_1$–$C_4$ alkoxy group, $C_1$–$C_4$ alkoxy-$C_1$–$C_4$ alkoxy group, $C_2$–$C_4$ alkenyloxy group, $C_2$–$C_4$ alkynyloxy group, amino group, $C_1$–$C_4$ alkylamino group, di-$C_1$–$C_4$ alkylamino group or anilino group which can be substituted with halogen atom or $C_1$–$C_4$ alkyl group.

9 Claims, No Drawings

HERBICIDAL PHENOXY-PHENOXYALKANE THIO ESTERS

This is a division, of application Ser. No. 722,327, filed Sept. 10, 1976 now U.S. Pat. No. 4,070,177.

BACKGROUND OF THE INVENTION

The present invention relates to phenoxy phenoxy alkane carboxylic acid derivatives and herbicide which contain the same.

SUMMARY OF THE INVENTION

It is an object of the present invention to provide novel compounds of phenoxy phenoxy alkane carboxylic acid derivatives.

It is the other object of the invention to provide herbicides which impart excellent herbicidal effect without phytotoxicity.

The phenoxy phenoxy alkane carboxylic acid derivatives are compounds having the formula

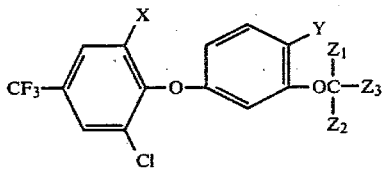

wherein X represents —H or —Cl; Y represents halogen atom or cyano group; $Z_1$ represents —H or methyl group; $Z_2$ represents —H, methyl or ethyl group; $Z_3$ represents cyano group or

group; R represents hydroxy group; —O— cation group, $C_1$–$C_4$ alkylthio group, $C_2$–$C_4$ alkenylthio group, $C_2$–$C_4$ alkynylthio group, $C_1$–$C_4$ alkoxy group, $C_1$–$C_4$ alkoxy-$C_1$–$C_4$ alkoxy group, $C_2$–$C_4$ alkenyloxy group, $C_2$–$C_4$ alkynyloxy group, amino group, $C_1$–$C_4$ alkylamino group, di-$C_1$–$C_4$ alkylamino group or anilino group which can be substituted with halogen atom or $C_1$–$C_4$ alkyl group.

The herbicides of the invention comprises at least one of the phenoxy phenoxy alkane carboxylic acid derivatives as active ingredient.

DETAILED DESCRIPTION OF THE PREFERRED EMBODIMENTS

In the formula of the phenoxy phenoxy alkane carboxylic acid derivatives, the halogen atom can be chlorine, bromine, iodine, etc.; the cation can be a salt forming atom such as sodium, potassium, magnesium, calcium or a salt forming residue such as ammonium group, organic amine etc.; the alkyl moiety in the $C_1$–$C_4$ alkylthio group, $C_1$–$C_4$ alkoxy group, $C_1$–$C_4$ alkoxy-$C_1$–$C_4$ alkoxy group, $C_1$–$C_4$ alkylamino group and di-$C_1$–$C_4$ alkylamino group can be methyl, ethyl, n-propyl, isopropyl and n-butyl group; the $C_2$–$C_4$ alkenyloxy group can be allyloxy group; the $C_2$–$C_4$ alkynyloxy group can be 2-propynyloxy group; the $C_2$–$C_4$ alkenylthio group can be allylthio group; the $C_2$–$C_4$ alkynylthio group can be 2-propynylthio group; the substituted anilino group can be 2-chloro anilino, 4-chloro anilino, 2-bromo anilino, 2-methyl anilino and 2-ethyl anilino group and the like.

The compounds having the formula

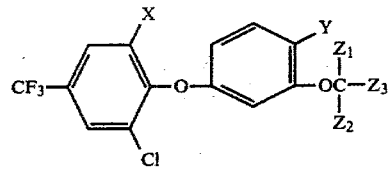

can be classified as follows.

(1) Phenoxy phenoxy propionic or acetic acid derivatives
X: —H
Y: halogen atom or —CN
$Z_1$: —H
$Z_2$: —H or —CH$_3$
$Z_3$: —COOH, —COOM or —COOR' (M: cation; R': $C_1$–$C_4$ alkyl group)

(2) Phenoxy phenoxy alkane nitrile
X: —H or —Cl
Y: halogen atom or —CN
$Z_1$: —H
$Z_2$: —H, —CH$_3$ or —C$_2$H$_5$
$Z_3$: —CN (3) Phenoxy phenoxy alkane carboxylic acid derivatives
X: —H or —Cl
Y: halogen atom or —CN
$Z_1$: —H or —CH$_3$
$Z_2$: —H, —CH$_3$ or —C$_2$H$_5$
$Z_3$: —COOR$_1$, COSR$_2$, CONR$_3$R$_4$ or

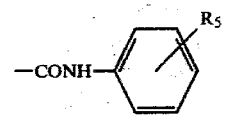

($R_1$: —H, salt forming atom, salt forming residue, $C_1$–$C_4$ alkyl, $C_1$–$C_4$ alkoxy, $C_1$–$C_4$ alkyl, $C_2$–$C_4$ alkenyl or $C_2$–$C_4$ alkynyl group;
$R_2$: $C_1$–$C_4$ alkyl, $C_2$–$C_4$ alkenyl or $C_2$–$C_4$ alkynyl group;
$R_3$, $R_4$: —H or $C_1$–$C_4$ alkyl group;
$R_5$: —H, halogen atom or $C_1$–$C_4$ alkyl group.)

The phenoxy phenoxy alkane carboxylic acid derivatives can be usually produced by the following processes.

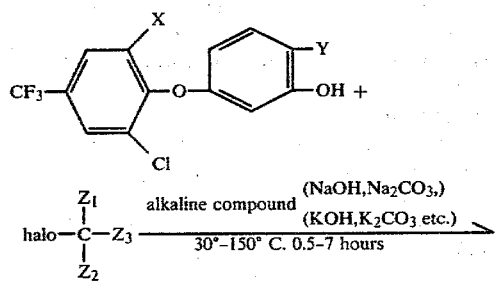

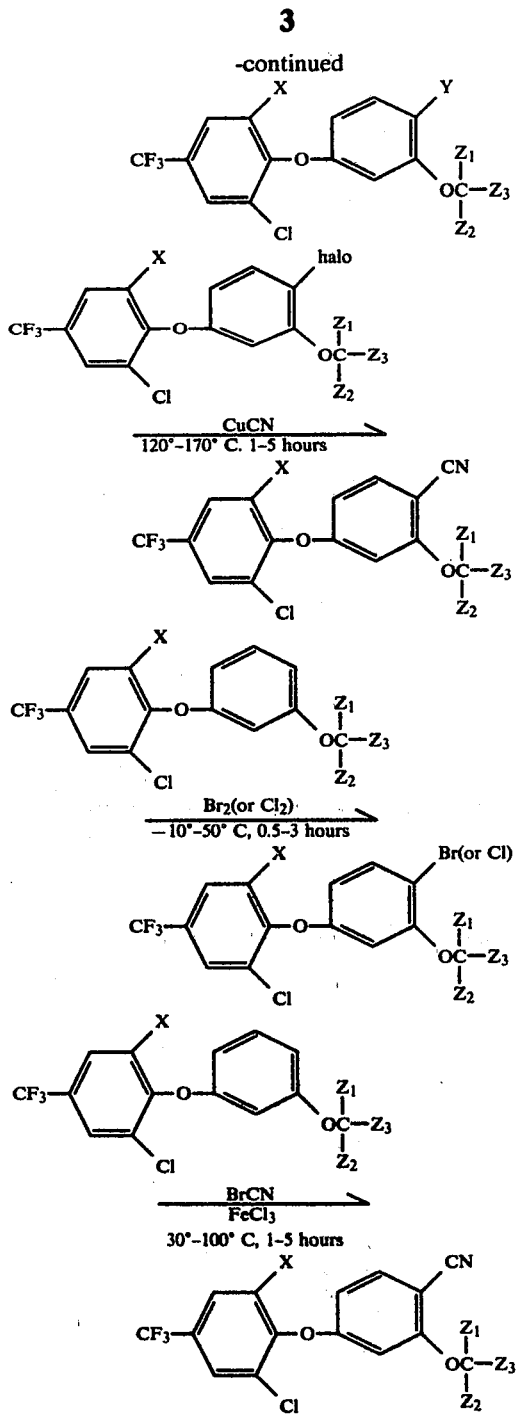

wherein X, Y, $Z_1$, $Z_2$ and $Z_3$ are defined above; and the term of halo represents halogen atom.

The resulting phenoxy phenoxy alkane carboxylic acid derivatives can be converted to the salts, esters or amides shown by the formula in accordance with the following processes.

In the following processes, the alkane carboxylic acids mean phenoxy phenoxy alkane carboxylic acid having the formula wherein $Z_3$ is carboxyl group.

Production of salts

A neutralization of the alkane carboxylic acid is conducted with an alkaline compound.

Production of esters (a) A condensation reaction or the alkane carboxylic acid and the alcohol corresponding to the object product is conducted in the presence of Lewis acid.

(b) A reaction of an alkane carbonyl halide converted from the alkane carboxylic acid with the alcohol corresponding to the object product is conducted in the presence of an alkaline compound.

(c) An ester-interchange reaction is conducted by using the ester converted from the alkane carboxylic acid.

Production of amides (a) A reaction of the alkane carboxylic acid and the amine corresponding to the object product is conducted in the presence of Lewis acid.

(b) A reaction of the alkane carbonyl halide converted from the alkane carboxylic acid with the amine corresponding to the object product is conducted.

(c) A hydrolysis of the alkane nitrile converted from the alkane carboxylic acid is conducted.

(d) A reaction of the ester converted from the alkane carboxylic acid with the amine corresponding to the object product is conducted.

The examples of preparations of the phenoxy phenoxy alkane carboxylic acid derivatives will be illustrated.

EXAMPLE 1

Preparation of methyl-α-[2-bromo-5-(2-chloro-4-trifluoromethyl phenoxy)phenoxy]propionate A 18 g of 2-bromo-5-(2-chloro-4-trifluoromethyl phenoxy)phenol and 12.5 g of methyl-α-bromo propionate were dissolved in 40 ml of methylethyl ketone. A 7 g of anhydrous potassium carbonate was added to the above solution and the reaction was conducted under reflux condition with stirring the mixture for 2 hours.

The reaction mixture was poured into suitable amount of water to form the oily product. The product was extracted with chloroform and the extract was washed with water and was dried. The chloroform was evaporated off and the product was distilled at reduced pressure to obtain 17 g of the object compound having a boiling point of 185° to 186° C./2.5 mmHg.

EXAMPLE 2

Preparation of methyl-α-[2-cyano-5-(2-chloro-4-trifluoromethyl phenoxy)phenoxy]propionate A 10 g of methyl-α-[2-bromo-5-(2-chloro-4-trifluoromethyl phenoxy)phenoxy]propionate produced in Example 1 was dissolved in 15 ml of dimethyl formamide, and 2.4 g of cuprous cyanide was added to the solution and the reaction was conducted under reflux condition with stirring the mixture for 5 hours.

The reaction mixture was poured into suitable amount of an aqueous solution of ferric chloride to form the oily product. The product was extracted with chloroform and the extract was washed with water and was dried. The chloroform was evaporated off and the product was distilled at reduced pressure to obtain 7.5 g of the object compound having a boiling point of 189° to 192° C./1.5 mmHg.

EXAMPLE 3

Preparation of α-[2-cyano-5-(2-chloro-4-trifluoromethyl phenoxy)phenoxy]propion amide A 10 g of methyl-α-[2-cyano-5-(2-chloro-4-trifluoromethyl phenoxy)phenoxy]propionate was dissolved in 20 ml of benzene. The solution was cooled at 0° C. and 10 g of 28% ammonia water was added dropwise to react them at room temperature for 2 hours. After the reaction, the benzene phase was separated and was washed with water. The benzene was distilled off and the product was recrystallized from methanol to obtain 5.5 g of the object compound having a melting point of 134° to 137° C.

EXAMPLE 4

Preparation of methyl-α-[2-bromo-5-(2-chloro-4-trifluoromethyl phenoxy)phenoxy]propionthioate A 4.0 g of α-[2-bromo-5-(2-chloro-4-trifluoromethyl phenoxy)phenoxy]propionyl chloride which was produced by using α-[2-bromo-5-(2-chloro-4-trifluoromethyl phenoxy)phenoxy]propionic acid was dissolved in 10 ml of benzene. A 5 g of 15% aqueous solution of sodium methyl mercaptan was added dropwise to the solution under cooling at 10° to 20° C. The reaction was conducted at the above temperature for 2 hours.

After the reaction, the benzene phase was separated and was washed with water and was dried. The benzene was distilled off and the product was distilled at reduced pressure to obtain 4 g of the object compound having a boiling point of 203° to 206° C./2 mmHg.

EXAMPLE 5

Preparation of ethyl-α-[2-cyano-5-(2-chloro-4-trifluoromethyl phenoxy)phenoxy]butyrate A 10 g of ethyl-α-[2-bromo-5-(2-chloro-4-trifluoromethyl phenoxy)phenoxy]butyrate was dissolved in 20 ml of dimethylformamide.

A 2.5 g of cuprous cyanide was added to the solution and the reaction was conducted at 145° to 150° C. for 4 hours with stirring the mixture.

The reaction mixture was poured into suitable amount of an aqueous solution of ferric chloride. The product was extracted with chloroform. The extract was washed with water and was dried. The chloroform was evaporated off and the product was distilled at reduced pressure to obtain 6 g of the object compound having a boiling point of 200° to 205° C./1 mmHg.

EXAMPLE 6

Preparation of ethyl-α-[2-bromo-5-(2-chloro-4-trifluoromethyl phenoxy)phenoxy]isobutyrate A 14.5 g of 2-bromo-5-(2-chloro-4-trifluoromethyl phenoxy)phenol and 10 g of ethyl-α-bromo isobutyrate were dissolved in 20 ml of methylethyl ketone. A 10 g of anhydrous potassium carbonate was added to the solution and the reaction was conducted under reflux condition with stirring the mixture for 2 hours.

The reaction mixture was poured into suitable amount of water.

The product was extracted with chloroform and the extract was washed with water. The chloroform was distilled off and the product was distilled at reduced pressure to obtain 16 g of the object compound having a boiling point of 178° to 180° C./2 mmHg.

EXAMPLE 7

Preparation of ethyl-α-[2-bromo-5-(2,6-dichloro-4-trifluoromethyl phenoxy)phenoxy]propionate A 19.5 g of 2-bromo-5-(2,6-dichloro-4-trifluoromethyl phenoxy)phenol and 12.5 g of methyl-α-bromo propionate were dissolved in 40 ml of methylethyl ketone. A 7 g of anhydrous potassium carbonate was added to the solution and the reaction was conducted under reflux condition with stirring the mixture for 2 hours.

The reaction mixture was poured into suitable amount of water.

The product was extracted with chloroform and the extract was washed with water and was dried. The chloroform was distilled off and the product was distilled at reduced pressure to obtain 20.7 g of the object compound having a boiling point of 198° to 203° C./1.5 mmHg.

EXAMPLE 8

Preparation of ethyl-α-[2-cyano-5-(2,6-dichloro-4-trifluoromethyl phenoxy)phenoxy]propionate A 15 g of ethyl-α-[2-bromo-5-(2,6-dichloro-4-trifluoromethyl phenoxy) phenoxy]propionate produced in Example 7 was dissolved in 25 ml of dimethylformamide. A 3 g of cuprous cyanide was added to the solution and the reaction was conducted under reflux condition for 4 hours with stirring the mixture.

The reaction mixture was poured into suitable amount of aqueous solution of ferric chloride. The product was extracted with chloroform and the extract was washed with water and was dried. The chloroform was distilled off and the product was distilled at reduced pressure to obtain 11 g of the object compound having a boiling point of 209° to 215° C./1 mmHg.

EXAMPLE 9

Preparation of α-[2-cyano-5-(2-chloro-4-trifluoromethyl phenoxy)phenoxy]butyronitrile A 10 g of α-[2-bromo-5-(2-chloro-4-trifluoromethyl phenoxy)phenoxy]butyronitrile was dissolved in 20 ml of dimethylformamide. A 2.5 g of cuprous cyanide was added to the solution and the reaction was conducted at 145° to 150° C. for 2 hours with stirring the mixture. The reaction mixture was cooled and was poured into suitable amount of aqueous solution of ferric chloride. The product was extracted with chloroform and the extract was washed with water and was dried. The chloroform was distilled off and the product was distilled at reduced pressure to obtain 7 g of the object compound having the boiling point of 202° to 207° C./2 mmHg.

Typical compounds prepared by the above processes are listed below. The compound numbers appearing below will be referred to later in the specification.

Compound No. 1: Methyl-2-bromo-5-(2-chloro-4-trifluoromethyl phenoxy)phenoxy acetate; bp 185°–190° C./2 mmHg Compound No. 2: Methyl-α-[2-bromo-5-(2-chloro-4-trifluoromethyl phenoxy)phenoxy]propionate; bp 185°–186° C./2.5 mmHg Compound No. 3: Ethyl-α-[2-bromo-5-(2-chloro-4-trifluoromethyl phenoxy)phenoxy]propionate; bp 200°–205° C./3 mmHg Compound No. 4: 2-bromo-5-(2-chloro-4-trifluoromethyl phenoxy)phenoxy acetic acid; mp 83°–89° C.

Compound No. 5: α-[2-bromo-5-(2-chloro-4-trifluoromethyl phenoxy)phenoxy]propionic acid; mp 109°–120° C.

Compound No. 6: Methyl-2-chloro-5-(2-chloro-4-trifluoromethyl phenoxy)phenoxy acetate; mp 106°–108° C.

Compound No. 7: Methyl-α-[2-chloro-5-(2-chloro-4-trifluoromethyl phenoxy)phenoxy]propionate; bp 167°–170° C./2 mmHg Compound No. 8: Methyl-α-[2-iodo-5-(2-chloro-4-trifluoromethyl phenoxy)phenoxy]propionate; bp 195°–200° C./2.5 mmHg Compound No. 9: Methyl-2-cyano-5-(2-chloro-4-trifluoromethyl phenoxy)phenoxy acetate; mp 137°–140° C.

Compound No. 10: Methyl-α-[2-cyano-5-(2-chloro-4-trifluoromethyl phenoxy)phenoxy]propionate; bp 189°–192° C./1.5 mmHg (mp 84°–86° C.)

Compound No. 11: Ethyl-α-[2-cyano-5-(2-chloro-4-trifluoromethyl phenoxy)phenoxy]propionate; bp 200°–205° C./3 mmHg Compound No. 12: 2-cyano-5-(2-chloro-4-trifluoromethyl phenoxy)phenoxy acetic acid; mp 91°–97° C.

Compound No. 13: α-[2-cyano-5-(2-chloro-4-trifluoromethyl phenoxy)phenoxy]propionic acid; mp 128°–133° C.

Compound No. 14: Sodium-α-[2-cyano-5-(2-chloro-4-trifluoromethyl phenoxy)phenoxy]propionate Compound No. 15: α-[2-cyano-5-(2-chloro-4-trifluoromethyl phenoxy)phenoxy]propionic acid dimethyl ammonium salt Compound No. 16: α-[2-cyano-5-(2-chloro-4-trifluoromethyl phenoxy)phenoxy]propionic acid triethanol ammonium salt Compound No. 17: Methyl-α-[2-bromo-5-(2-chloro-4-trifluoromethyl phenoxy)phenoxy]propionthioate; bp 203°–206° C./2 mmHg Compound No. 18: n-Propyl-α-[2-bromo-5-(2-chloro-4-trifluoromethyl phenoxy)phenoxy]butyrthioate; bp 205°–210° C./2 mmHg Compound No. 19: Allyl-α-[2-bromo-5-(2-chloro-4-trifluoromethyl phenoxy)phenoxy]butyrthioate Compound No. 20: α-[2-bromo-5-(2-chloro-4-trifluoromethyl phenoxy)phenoxy]propionamide; mp 129°–135° C.

Compound No. 21: N-ethyl-α-[2-bromo-5-(2-chloro-4-trifluoromethyl phenoxy)phenoxy]propionamide; mp 105°–107° C.

Compound No. 22: α-[2-chloro-5-(2-chloro-4-trifluoromethyl phenoxy)phenoxy]propionamide; mp 123°–127° C.

Compound No. 23: Methoxyethyl-α-[2-cyano-5-(2-chloro-4-trifluoromethyl phenoxy)phenoxy]priopionate; bp 201°–205° C./1.5 mmHg Compound No. 24: Allyl-α-[2-cyano-5-(2-chloro-4-trifluoromethyl phenoxy)phenoxy]propionate; bp 185°–190° C./0.5 mmHg Compound No. 25: Allyl-α-[2-cyano-5-(2-chloro-4-trifluoromethyl phenoxy)phenoxy]butyrate; bp 201°–204° C./2 mmHg Compound No. 26: 2-propynyl-α-[2-cyano-5-(2-chloro-4-trifluoromethyl phenoxy)phenoxy]butyrate Compound No. 27: Methyl-α-[2-cyano-5-(2-chloro-4-trifluoromethyl phenoxy)phenoxy]propionthioate; bp 185°–190° C./1.5 mmHg Compound No. 28: Ethyl-α-[2-cyano-5-(2-chloro-4-trifluoromethyl phenoxy)phenoxy] propionthioate; bp 203°–210° C./2 mmHg Compound No. 29: α-[2-cyano-5-(2-chloro-4-trifluoromethyl phenoxy)phenoxy]propionamide; mp 134°–137° C.

Compound No. 30: N,N-diethyl-α-[2-cyano-5-(2-chloro-4-trifluoromethyl phenoxy)phenoxy]propionamide; mp 70°–75° C.

Compound No. 31: α-[2-cyano-5-(2-chloro-4-trifluoromethyl phenoxy)phenoxy]butyramide; mp 138°–140° C.

Compound No. 32: N,N-dimethyl-α-[2-cyano-5-(2-chloro-4-trifluoromethyl phenoxy)phenoxy]butyramide; mp 102°–107° C.

Compound No. 33: α-[2-cyano-5-(2-chloro-4-trifluoromethyl phenoxy)phenoxy]propion-o-bromo anilide; mp 135°–138° C.

Compound No. 34: α-[2-cyano-5-(2-chloro-4-trifluoromethyl phenoxy)phenoxy]propion-o-methyl anilide; mp 107°–111° C.

Compound No. 35: α-[2-cyano-5-(2-chloro-4-trifluoromethyl phenoxy)phenoxy]propion-o-ethyl anilide; mp 153°–155° C.

Compound No. 36: α-[2-cyano-5-(2-chloro-4-trifluoromethyl phenoxy)phenoxy]butyr-o-chloro anilide Compound No. 37: Ethyl-α-[2-bromo-5-(2-chloro-4-trifluoromethyl phenoxy)phenoxy]butyrate; bp 182°–185° C./1.5 mmHg Compound No. 38: Sodium-α-[2-bromo-5-(2-chloro-4-trifluoromethyl phenoxy)phenoxy]butyrate Compound No. 39: Isopropyl-α-[2-chloro-5-(2-chloro-4-trifluoromethyl phenoxy)phenoxy]butyrate; bp 176°–179° C./2 mmHg Compound No. 40: Ethyl-α-[2-iodo-5-(2-chloro-4-trifluoromethyl phenoxy)phenoxy]butyrate; bp 190°–200° C./2 mmHg Compound No. 41: Methyl-α-[2-cyano-5-(2-chloro-4-trifluoromethyl phenoxy)phenoxy]butyrate; bp 119°–203° C./1 mmHg Compound No. 42: Ethyl-α-[2-cyano-5-(2-chloro-4-trifluoromethyl phenoxy)phenoxy]butyrate; bp 200°–205° C./1 mmHg Compound No. 43: α-[2-cyano-5-(2-chloro-4-trifluoromethyl phenoxy)phenoxy]butyric acid; mp 121°–127° C.

Compound No. 44: Potassium-α-[2-cyano-5-(2-chloro-4-trifluoromethyl phenoxy)phenoxy]butyrate Compound No. 45: α-[2-cyano-5-(2-chloro-4-trifluoromethyl phenoxy)phenoxy]butyric acid ammonium salt Compound No. 46: Ethyl-α-[2-bromo-5-(2-chloro-4-trifluoromethyl phenoxy)phenoxy]isobutyrate; bp 178°–180° C./2 mmHg Compound No. 47: α-[2-bromo-5-(2-chloro-4-trifluoromethyl phenoxy)phenoxy]isobutyric acid; mp 113°–117° C.

Compound No. 48: Ethyl-α-[2-cyano-5-(2-chloro-4-trifluoromethyl phenoxy)phenoxy]isobutyrate; bp 190°–195° C./1 mmHg Compound No. 49: Methyl-α-[2-cyano-5-(2-chloro-4-trifluoromethyl phenoxy)phenoxy]isobutyrthioate Compound No. 50: Allyl-α-[2-cyano-5-(2-chloro-4-trifluoromethyl phenoxy)phenoxy]isobutyrate Compound No. 51: α-[2-cyano-5-(2-chloro-4-trifluoromethyl phenoxy)phenoxy]isobutyric acid; mp135°–140° C.

Compound No. 52: Sodium-α-[2-cyano-5-(2-chloro-4-trifluoromethyl phenoxy)phenoxy]istobutyrate Compound No. 53: Methyl-2-cyano-5-(2,6-dichloro-4-trifluoromethyl phenoxy)phenoxy acetate; bp190°–195° C./1 mmHg Compound No. 54: α-[2-bromo-5-(2,6-dichloro-4-trifluoromethyl phenoxy)phenoxy]propionic acid; mp113°–119° C.

Compound No. 55: Ethyl-α-[2-bromo-5-(2,6-dichloro-4-trifluoromethyl phenoxy)phenoxy]propionate; bp198°–203° C/1.5 mmHg Compound No. 56: Ethyl-α-[2-cyano-5-(2,6-dichloro-4-trifluoromethyl phenoxy)phenoxy]propionate; bp209°–215° C./1 mmHg Compound No. 57: α-[2-cyano-5-(2,6-dichloro-4-trifluoromethyl phenoxy)phenoxy]propion amide; mp144°–151° C.

Compound No. 58: Methyl-α-[2-cyano-5-(2,6-dichloro-4-trifluoromethyl phenoxy)phenoxy]butyrate; bp212°–217° C./1 mmHg Compound No. 59: Methyl-α-[2-bromo-5-(2,6-dichloro-4-trifluoromethyl phenoxy)phenoxy]propionate; bp195°–200° C./4 mmHg Compound No. 60: Methyl-α-[2-cyano-5-(2,6-dichloro-4-trifluoromethyl phenoxy)phenoxy]propionate; bp220°–226° C./3 mmHg Compound No. 61: α-[2-cyano-5-(2-chloro-4-trifluoromethyl phenoxy)phenoxy]butyronitrile; bp202°–207° C./2 mmHg Compound No. 62: α-[2-cyano-5-(2-chloro-4-trifluoromethyl phenoxy)phenoxy]propionitrile; mp144°–146° C.

Compound No. 63: α-[2-cyano-5-(2-chloro-4-trifluoromethyl phenoxy)phenoxy]Isovaleronitrile; bp199°–203° C./1 mmHg Compound No. 64: α-2-cyano-5-(2-chloro-4-trifluoromethyl phenoxy)phenoxy acetonitrile Compound No. 65: α-[2-cyano-5-(2,6-dichloro-4-trifluoromethyl phenoxy)phnoxy]propionitrile; bp207°–211° C./1.5 mmHg Compound No. 66: α-[2-bromo-5-(2-chloro-4-trifluoromethyl phenoxy)phenoxy]propionitrile; bp190°–192° C./2.5 mmHg Compound No. 67: α-[2-bromo-5-(2-chloro-4-trifluoromethyl phenoxy)phenoxy]butyronitrile; bp195°–200° C./2.5 mmHg Compound No. 68: α-2-bromo-5(2-chloro-4-trifluoromethyl phenoxy)phenoxy acetonitrile; mp110°–112° C.

Compound No. 69: α-[2-bromo-5-(2,6-dichloro-4-trifluoromethyl phenoxy)phenoxy]propionitrile Compound No. 70: α-[2-chloro-5-(2-chloro-4-trifluoromethyl phenoxy)phenoxy]propionitrile; bp183°–188° C./2 mmHg Compound No. 71: α-[2-iodo-5-(2-chloro-4-trifluoromethyl phenoxy)phenoxy]butyronitrile; bp195°–202° C./2 mmHg The phenoxy phenoxy alkane carboxylic acid derivatives of the invention impart excellent effects when they are used as active ingredients of herbicide as shown in the following test Experiments.

The main effects are as follows.

In the application of the compounds in the upland farm, (1) noxious weeds can be killed by the foliar treatment in low concentration of the active ingredient;

(2) the growth inhibiting effect to broad leaved weeds is higher than that of the gramineous plant and accordingly, noxious broad leaved weeds can be controlled in plantation of gramineous crops such as wheat and rice plants; and (3) excellent herbicidal effects which are superior to the conventional herbicides having analogous structures in the soil treatment. In the application of the compounds in the paddy field (low land field), (4) satisfactory herbicidal effect can be imparted to arrowhead, bulrush and others which are remarkably grown in recent years; and (5) barnyard grass can be controlled without phytotoxicity to rice plant.

The herbicides of the invention are remarkably suitable for selectively killing broad leaved weeds in plantation of gramineous crops from the viewpoints of the activity. Thus, the herbicides of the invention have excellent herbicidal effect to various weeds and they can be applied to upland farm as well as orchards, mulberry field, paddy field (low land field), forests, ridges, grounds, factory sites, etc. The herbicides can be selectively used for the foliar treatment and the soil treatment.

The active ingredients of the invention can be used in the form of aqueous solutions or aqueous dispersions which are prepared by dissolving or dispersing the active ingredient of the phenoxy phenoxy alkene carboxylic acid derivative.

The active ingredients of the invention can be also used in the form of emulsifiable concentrates, wettable powder, water miscible solution, dusts, and granules which are prepared by mixing the active ingredient with carriers such as diatomaceous earth, calcium hydroxide, calcium carbonate, talc, whitecarbon, kaolin, bentonite, Jeeklite or solvents such as n-hexane, toluene, xylene, solvent naphtha, ethanol, dioxane, acetone, isophorone, methyl isobutyl ketone, dimethylformamide, dimethyl sulfoxide, water, if desired;

anionic or nonionic surface active agents such as sodium alkylsulfate, sodium alkylbenzenesulfonate, sodium ligninsulfonate, polyoxyethylene lauryl ether, polyoxyethylene alkylaryl ether, polyoxyethylene fatty acid ester, polyoxyethylene sorbitan fatty acid ester and the like. The herbicidal compositions usually comprises 1 to 90 wt.% preferably 1 to 70 wt.% of the active ingredient; 5 to 99 wt.% preferably 25 to 99 wt.% of the carrier or solvent, and 0 to 30 wt.% preferably 1 to 20 wt.% of the surface active agent.

The active ingredient can be combined with other agricultural chemicals such as herbicides, insecticides, fungicides or fertilizers or soils. In some cases, synergistic effect may be obtained. Suitable amount of the herbicide of the invention is dependent upon the conditions of weather or soil, form of the composition, time of application, method of application and kinds of weeds, etc. and is usually in a range of 0.1 to 100 g preferably 0.5 to 70 g per 1 are.

Typical composition will be illustrated.

Composition 1

(1) Methyl-α-[2-cyano-5-(2-chloro-4-trifluoromethyl phenoxy)phenoxy]propionate: 20 wt. parts
(2) Xylene: 60 wt. parts
(3) Sorpol 2806B: 20 wt. parts The components (1)–(3) were uniformly mixed to give emulsifiable concentrate of the herbicidal composition of the invention.

Composition 2

(1) Jeeklite: 78 wt. parts
(2) Lavelin S: 2 wt. parts
(3) Sorpol 5039: 5 wt. parts
(4) Carplex: 15 wt. parts The mixture of these components (1)–(4) was mixed with methyl-α-[2-bromo-5-(2-chloro-4-trifluoromethyl phenoxy)phenoxy]propionate at a ratio of 4:1 by weight to give the wettable powder of the herbicidal composition of the invention.

Composition 3

(1) N-ethyl-α-[2-bromo-5-(2-chloro-4-trifluoromethyl phenoxy)phenoxy]propionamide: 20 wt. parts
(2) Jeeklite: 75 wt. parts
(3) Sodium lignin sulfonate: 3 wt. parts
(4) Lavelin S: 2 wt. parts The components (1)–(4) were uniformly mixed to give wettable powder of the herbicidal composition of the invention.

Composition 4

(1) α-[2-cyano-5-(2-chloro-4-trifluoromethyl phenoxy)phenoxy]butyramide: 3 wt. parts
(2) Kaolin powder: 50 wt. parts
(3) Talc: 46 wt. parts
(4) Sodium lignin sulfonate: 1 wt. part The components (1)–(4) were uniformly mixed and crushed to give dusts of the herbicidal composition of the invention.

Composition 5

(1) Ethyl-α-[2-bromo-5-(2-chloro-4-trifluoromethyl phenoxy)phenoxy]butyrate: 20 wt. parts
(2) N-methyl-2-pyrrolidone: 15 wt. parts
(3) Polyoxyethylene alkylaryl ether: 5 wt. parts
(4) Ethanol: 60 wt. parts The components (1)–(4) were uniformly mixed to give water miscible solution of the herbicidal composition of the invention.

Composition 6

(1) Ethyl-α-[2-cyano-5-(2-chloro-4-trifluoromethyl phenoxy)phenoxy]isobutyrate: 15 wt. parts
(2) Xylene: 65 wt. parts
(3) Polyoxyethylene stearate: 20 wt. parts The components (1)–(3) were uniformly mixed to give emulsifiable concentrate of the herbicidal composition of the invention.

Composition 7

(1) Bentonite: 58 wt. parts
(2) Jeeklite: 30 wt. parts
(3) Sodium lignin sulfonate: 5 wt. parts The components (1)–(3) were mixed and granulated. A solution prepared by diluting ethyl-α-[2-cyano-5-(2,6-dichloro-4-trifluoromethyl phenoxy)phenoxy]propionate with acetone was sprayed on said granulated components to give the granules of the herbicidal composition of the invention.

Composition 8

(1) α-[2-cyano-5-(2,6-dichloro-4-trifluoromethyl phenoxy)phenoxy]propionitrile: 7 wt. parts
(2) Jeeklite: 30 wt. parts
(3) Bentonite: 60 wt. parts
(4) Sodium lignin sulfonate: 3 wt. parts The components (1)–(4) were mixed and granulated with suitable amount of water to give granules of the herbicidal composition of the invention.

Note

Sorpol 2806B

A mixture of a polyoxyethylene phenyl phenol derivative, a polyoxyethylene alkylaryl ether, a polyoxyethylene sorbitan alkylate and an alkylaryl sulfonate produced by Toho Chemical Co., Ltd.

Levelin S

A sodium naphthalene sulfonate-formaldehyde condensate produced by Daiichi Kogyo Seiyaku Co., Ltd.

Sorpol 5039

A sulfate of polyoxyethylene alkylaryl ether produced by Toho Chemical Co., Ltd.

Carplex

White carbon ($SiO_2 \cdot nH_2O$) produced by Shionogi Seiyaku Co., Ltd.

Experiments of the herbicides of the invention will be illustrated. The active ingredient used are shown by the above-mentioned compound numbers.

EXPERIMENT 1

Each pot of 1/10,000 Are (Are = 100 m$^2$) was filled with soil and the soil was supersaturated with water.

A specific amount of air-dried barnyard grass seeds were sown in the pot and covered with soil.

When the barnyard grass appeared on the surface of the soil, water was poured into each pot to a depth of 3 cm in the flooded condition and then an aqueous dispersion of each of active ingredients was poured into the pot.

Fourteen days after the treatment, the weeds which had survived was taken up, air-dried and weighed.

The results are shown in Table 1 in percent by weight of the weeds which survived in the treated pot versus in the untreated pot and are indicated as "Degree of Growth".

TABLE 1

| Active ingredient (Compound No.) | Degree of growth (%) Amount of active ingredient (g/a) | |
|---|---|---|
| | 10 | 5 |
| 1 | 0 | 0 |
| 2 | 0 | 0 |
| 3 | 0 | 0 |
| 4 | 0 | 4 |
| 5 | 0 | 0 |
| 6 | 0 | 18 |
| 7 | 0 | 9 |
| 8 | 0 | 0 |
| 9 | 0 | 0 |
| 10 | 0 | 0 |
| 11 | 0 | 0 |
| 12 | 0 | 0 |
| 13 | 0 | 0 |
| 14 | 0 | 0 |

TABLE 1-continued

| Active ingredient (Compound No.) | Degree of growth (%) Amount of active ingredient (g/a) | |
|---|---|---|
| | 10 | 5 |
| 17 | 0 | 0 |
| 18 | 0 | 9 |
| 20 | 0 | 0 |
| 21 | 0 | 0 |
| 22 | 0 | 7 |
| 23 | 0 | 0 |
| 24 | 0 | 0 |
| 25 | 0 | 0 |
| 27 | 0 | 0 |
| 28 | 0 | 0 |
| 29 | 0 | 0 |
| 30 | 0 | 0 |
| 31 | 0 | 0 |
| 32 | 0 | 0 |
| 33 | 0 | 0 |
| 34 | 0 | 0 |
| 35 | 0 | 6 |
| 37 | 0 | 0 |
| 38 | 0 | 0 |
| 39 | 3 | 15 |
| 40 | 4 | 11 |
| 41 | 0 | 0 |
| 42 | 0 | 0 |
| 43 | 0 | 0 |
| 44 | 0 | 0 |
| 45 | 0 | 0 |
| 46 | 0 | 3 |
| 47 | 0 | 13 |
| 48 | 0 | 0 |
| 51 | 0 | 4 |
| 52 | 0 | 6 |
| 53 | 0 | 0 |
| 54 | 0 | 0 |
| 55 | 0 | 0 |
| 56 | 0 | 0 |
| 57 | 0 | 0 |
| 58 | 0 | 0 |
| 61 | 0 | 0 |
| 62 | 0 | 0 |
| 63 | 0 | 11 |
| 64 | 0 | 0 |
| 65 | 0 | 0 |
| 66 | 0 | 0 |
| 67 | 0 | 0 |
| 68 | 0 | 0 |
| 70 | 0 | 0 |
| 71 | 0 | 0 |

EXPERIMENT 2

Each pot of 1/10,000 Are was filled with soil and the soil was supersaturated with water. A soil containing specific amounts of seeds of weeds were placed to cover the surface of soil. Water was poured into each pot to a depth of 3 cm. Seven days after this treatment, an aqueous dispersion of each active ingredients were sprayed on the soil.

Fourteen days after this treatment, the growth conditions of weeds were observed.

The results are shown in Table 2. In the Table, "Degree of growth control" is shown by 5 ratings as the following standards.

5: Complete growth suppression is found
4: Remarkable growth suppression is found
3: About 60% growth suppression compared with untreated plant is found
2: About 30% growth suppression compared with untreated plant is found
1: No apparent difference between treated plants and untreated plants is found.

TABLE 2

| Active ingredient (Compound No.) | Amount of active ingredient (g/a) | Degree of growth control | | | |
|---|---|---|---|---|---|
| | | Toothcup Long Stemmed Water-wort | Mono-choria | Bul-rush | Chufa |
| 1 | 10 | 5 | 5 | 5 | 5 |
| | 5 | 5 | 5 | 3 | 5 |
| 2 | 10 | 5 | 5 | 5 | 5 |
| | 5 | 5 | 5 | 5 | 5 |
| 3 | 10 | 5 | 5 | 5 | 5 |
| | 5 | 5 | 5 | 5 | 5 |
| 5 | 10 | 5 | 5 | 5 | 5 |
| | 5 | 5 | 5 | 4 | 5 |
| 6 | 10 | 5 | 5 | 4 | 4 |
| | 5 | 5 | 2 | — | 3 |
| 8 | 10 | 5 | 5 | 5 | 4-5 |
| | 5 | 5 | 5 | 5 | 5 |
| 9 | 10 | 5 | 5 | 5 | 5 |
| | 5 | 5 | 5 | 4 | 5 |
| 10 | 10 | 5 | 5 | 5 | 5 |
| | 5 | 5 | 5 | 5 | 5 |
| 11 | 10 | 5 | 5 | 5 | 5 |
| | 5 | 5 | 5 | 5 | 5 |
| 13 | 10 | 5 | 5 | 5 | 5 |
| | 5 | 5 | 5 | 5 | 5 |
| 14 | 10 | 5 | 5 | 5 | 5 |
| | 5 | 5 | 5 | 5 | 5 |
| 17 | 10 | 5 | 5 | 5 | 5 |
| | 5 | 5 | 5 | 4 | 5 |
| 20 | 10 | 5 | 5 | 4 | 5 |
| | 5 | 5 | 5 | 4-5 | 5 |
| 21 | 10 | 5 | 5 | 5 | 5 |
| | 5 | 5 | 5 | 3 | 5 |
| 24 | 10 | 5 | 5 | 5 | 5 |
| | 5 | 5 | 5 | 5 | 5 |
| 27 | 10 | 5 | 5 | 5 | 5 |
| | 5 | 5 | 5 | 5 | 5 |
| 28 | 10 | 5 | 5 | 5 | 5 |
| | 5 | 5 | 5 | 5 | 5 |
| 29 | 10 | 5 | 5 | 5 | 5 |
| | 5 | 5 | 5 | 5 | 5 |
| 30 | 10 | 5 | 5 | 5 | 5 |
| | 5 | 5 | 5 | 4 | 5 |
| 33 | 10 | 5 | 5 | 5 | 5 |
| | 5 | 5 | 5 | 5 | 5 |
| 34 | 10 | 5 | 5 | 4 | 5 |
| | 5 | 5 | 5 | 5 | 5 |
| 35 | 10 | 5 | 5 | 4 | 5 |
| | 5 | 5 | 3 | 2 | 4 |
| 37 | 10 | 5 | 5 | 5 | 4-5 |
| | 5 | 5 | 5 | 3 | 5 |
| 40 | 10 | 5 | 5 | 5 | 5 |
| | 5 | 5 | 5 | 5 | 5 |
| 42 | 5 | 5 | 5 | 5 | 5 |

TABLE 2-continued

| Active ingredient (Compound No.) | Amount of active ingredient (g/a) | Toothcup Long Stemmed Waterwort | Monochoria | Bulrush | Chufa |
|---|---|---|---|---|---|
| 46 | 10 | 5 | 5 | 3 | 5 |
|  | 5 | 5 | 5 | 2 | 3 |
| 48 | 10 | 5 | 5 | 4 | 5 |
|  | 5 | 5 | 5 | 3 | 5 |

EXPERIMENT 3

Each pot of 1/3,000 Are was filled with soil in an up-land condition and specific amounts of seeds of barnyard grass and radish were sown in the pot. The seeds were covered to a depth of about 1 cm with soil containing seeds of weeds such as Large crab-grass (Digitaria adscendens HENR),
Chickweed (Stellaria media VILL),
Bog stitchwort (Stellaria Alsine GRIMM var undulata OHWI),
Green foxtail (Setaria viridis BEAUV),
Wavy bittercress (Cardamine flexuosa WITH),
Chenopodium album L,
Pale smartweed (Polygonum lapathiofolium L.),
Cyperus esculentus L. and
Common groundsel (Senecio vulgaris L.).

Three days after sowing, an aqueous dispersion of each of active ingredients was sprayed on the surface of soil.

Twenty days after the treatment, the growth conditions of weeds were observed. The results are shown in Table 3. In the Table "Degree of growth control" is shown by 10 ratings wherein 10 designates complete growth suppression and 1 designates no apparent difference between treated plants and untreated plants.

TABLE 3

| Active ingredient (Compound No.) | Amount of active ingredient (g/a) | Barnyard grass | Radish | Weed |
|---|---|---|---|---|
| 1 | 100 | 8 | 9 | 10 |
|  | 50 | 6 | 6 | 10 |
| 2 | 100 | 10 | 10 | 10 |
|  | 50 | 10 | 10 | 10 |
| 3 | 100 | 10 | 10 | 10 |
|  | 50 | 10 | 10 | 10 |
| 5 | 100 | 10 | 10 | 10 |
|  | 50 | 10 | 10 | 10 |
| 8 | 100 | 7 | 9 | 10 |
|  | 50 | 7 | 5 | 10 |
| 9 | 100 | 8 | 9 | 10 |
|  | 50 | 6 | 6 | 10 |
| 10 | 100 | 10 | 10 | 10 |
|  | 50 | 10 | 10 | 10 |
| 11 | 100 | 10 | 10 | 10 |
|  | 50 | 10 | 10 | 10 |
| 13 | 100 | 10 | 10 | 10 |
|  | 50 | 10 | 10 | 10 |
| 20 | 100 | 9 | 7 | 10 |
|  | 50 | 8 | 7 | 10 |
| 21 | 100 | 8 | 8 | 10 |
|  | 50 | 7 | 8 | 9 |
| 24 | 100 | 10 | 10 | 10 |
|  | 50 | 10 | 8 | 10 |
| 27 | 100 | 10 | 10 | 10 |
|  | 50 | 10 | 10 | 10 |
| 28 | 100 | 10 | 9 | 10 |
|  | 50 | 8 | 4 | 10 |
| 29 | 100 | 10 | 10 | 10 |
|  | 50 | 10 | 10 | 10 |
| 30 | 100 | 10 | 10 | 10 |
|  | 50 | 9 | 10 | 10 |
| 33 | 100 | 10 | 10 | 10 |
|  | 50 | 9 | 10 | 10 |
| 34 | 100 | 10 | 10 | 10 |
|  | 50 | 8 | 10 | 10 |
| 35 | 100 | 6 | 10 | 10 |
|  | 50 | 5 | 10 | 10 |
| 37 | 100 | 7 | 10 | 10 |
|  | 50 | 6 | 9 | 10 |
| 42 | 100 | 10 | 10 | 10 |
|  | 50 | 10 | 10 | 10 |
| 46 | 100 | 7 | 10 | 10 |
|  | 50 | 6 | 10 | 10 |
| 48 | 100 | 8 | 10 | 10 |
|  | 50 | 7 | 9 | 10 |
| 59 | 100 | 10 | 10 | 10 |
|  | 50 | 10 | 10 | 10 |
| 60 | 100 | 10 | 10 | 10 |
|  | 50 | 10 | 10 | 10 |
| 61 | 100 | 9 | 10 | 10 |
|  | 50 | 7 | 7 | 10 |

EXPERIMENT 4

Each pot of 1/10,000 Are was filled with soil in an up-land condition and specific amounts of seeds of barnyard grass, radish and soy beans were sown in the pot. The seeds were covered to a depth of about 1 cm with soil. When the barnyard grass grew to two leaves stage, a specific concentration of an aqueous dispersion of each of active ingredient was uniformly sprayed on the leaves and stems.

Twenty days after the treatment, the growth conditions of the plants were observed.

The results are shown in Table 4 by the ratings of "Degree of growth control" of Experiment 3.

TABLE 4

| Active ingredient (Compound No.) | Concentration of active ingredient (ppm) | Barnyard grass | Radish | Soy beans |
|---|---|---|---|---|
| 1 | 250 | 5 | 10 | 10 |
|  | 125 | 4 | 10 | 8 |
|  | 62.5 | 3 | 9 | 6 |
| 2 | 250 | 7 | 10 | 10 |
|  | 125 | 5 | 10 | 10 |
|  | 62.5 | 4 | 10 | 8 |
| 9 | 250 | 5 | 10 | 9 |
|  | 125 | 4 | 9 | 7 |
|  | 62.5 | 3 | 8 | 6 |
| 10 | 250 | 9 | 10 | 10 |
|  | 125 | 8 | 10 | 10 |
|  | 62.5 | 7 | 10 | 10 |
| 3 | 2000 | 10 | 10 | 10 |
|  | 1000 | 10 | 10 | 10 |
|  | 2000 | 10 | 10 | 10 |
| 5 | 1000 | 8 | 10 | 10 |
|  | 2000 | 7 | 10 | 8 |
| 7 | 1000 | 6 | 10 | 7 |
|  | 2000 | 8 | 10 | 10 |
| 8 | 1000 | 7 | 10 | 10 |
|  | 2000 | 10 | 10 | 10 |
| 11 | 1000 | 10 | 10 | 10 |
|  | 2000 | 10 | 10 | 10 |
| 17 | 1000 | 10 | 10 | 10 |
|  | 2000 | 10 | 10 | 10 |
| 20 | 1000 | 7 | 10 | 10 |
|  | 2000 | 5 | 10 | 8 |
| 21 | 1000 | 5 | 7 | 6 |
|  | 2000 | 10 | 10 | 10 |
| 24 | 1000 | 10 | 10 | 10 |
|  | 2000 | 10 | 10 | 10 |
| 27 | 1000 | 10 | 10 | 10 |
|  | 2000 | 10 | 10 | 9 |
| 28 | 1000 | 10 | 8 | 7 |
|  | 2000 | 10 | 10 | 10 |
| 29 | 1000 | 10 | 10 | 10 |
|  | 2000 | 10 | 10 | 10 |
| 30 | 1000 | 10 | 10 | 10 |
|  | 2000 | 10 | 10 | 10 |
| 33 | 1000 | 9 | 10 | 10 |
|  | 2000 | 10 | 10 | 10 |
| 34 | 1000 | 9 | 10 | 10 |
|  | 2000 | 10 | 10 | 10 |
| 35 | 1000 | 8 | 10 | 8 |
|  | 2000 | 10 | 10 | 10 |
| 37 | 1000 | 10 | 10 | 10 |
|  | 2000 | 9 | 10 | 7 |
| 40 | 1000 | 8 | 10 | 7 |
|  | 2000 | 10 | 10 | 10 |
| 42 | 1000 | 10 | 10 | 10 |
|  | 2000 | 4 | 10 | 9 |
| 46 | 1000 | 4 | 10 | 7 |
|  | 2000 | 7 | 10 | 7 |
| 48 | 1000 | 5 | 10 | 6 |
|  | 2000 | 10 | 10 | 10 |
| 59 | 1000 | 10 | 10 | 10 |
|  | 2000 | 10 | 10 | 10 |
| 60 | 1000 | 10 | 10 | 10 |
|  | 2000 | 10 | 10 | 10 |
| 61 | 1000 | 7 | 10 | 10 |
|  | 2000 | 7 | 10 | 7 |
| 67 | 1000 | 5 | 10 | 5 |

What is claimed is:

1. A compound having the formula:

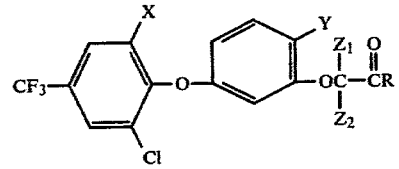

wherein
X represents hydrogen or chlorine;
Y represents halogen or cyano;
$Z_1$ represents hydrogen or methyl;
$Z_2$ represents hydrogen, methyl or ethyl; and R is $C_1$–$C_4$ alkylthio, $C_2$–$C_4$ alkenylthio or $C_2$–$C_4$ alkynylthio.

2. The compound of claim 1, wherein X is H or Cl; Y is bromine or cyano; $Z_1$ is hydrogen, $Z_2$ is methyl or ethyl and R is $C_1$–$C_4$ alkylthio, $C_2$–$C_4$ alkenylthio or $C_2$–$C_4$ alkynylthio.

3. The compound of claim 1, wherein X is H; Y is bromine or cyano, $Z_1$ is H; $Z_2$ is methyl or ethyl and R is $C_1$–$C_4$ alkylthio.

4. The compound of claim 3, wherein Y is bromine.

5. The compound of claim 3, wherein Y is cyano.

6. The compound of claim 3, wherein said compound is methyl-α-[2-bromo-5-(2-chloro-4-trifluoromethylphenoxy)phenoxy]propionthioate.

7. The compound of claim 3, wherein said compound is methyl-α-[2-cyano-5-(2-chloro-4-trifluoromethylphenoxy)phenoxy]propionthioate.

8. The compound of claim 3, wherein said compound is ethyl-α-[2-cyano-5-(2-chloro-4-trifluoromethylphenoxy)phenoxy]propionthioate.

9. A herbicidal composition, which comprises: the compound of claim 1 and an agriculturally acceptable adjuvant.

* * * * *